United States Patent [19]

Fukasawa

[11] Patent Number: 4,577,966

[45] Date of Patent: Mar. 25, 1986

[54] SPECTROPHOTOMETER

[75] Inventor: Yoshiro Fukasawa, Tokyo, Japan

[73] Assignee: Japan Spectroscopic Co., Ltd., Hachioji, Japan

[21] Appl. No.: 578,758

[22] Filed: Feb. 9, 1984

[30] Foreign Application Priority Data

Feb. 12, 1983 [JP] Japan .................................. 58-21949

[51] Int. Cl.[4] .......................... G01J 3/08; G01J 3/42
[52] U.S. Cl. .................................... 356/325; 250/343; 250/351
[58] Field of Search .................. 356/323, 324, 325; 250/343, 347, 351, 352, 353

[56] References Cited

U.S. PATENT DOCUMENTS 3,521,958  7/1970  Treharne ........................ 356/323
3,542,480 11/1970  Ford .............................. 356/323

Primary Examiner—Vincent P. McGraw
Attorney, Agent, or Firm—Wenderoth, Lind & Ponack

[57] ABSTRACT

A double-beam spectrophotometer for spectral analysis of a sample in the infrared region is provided in which to eliminate errors in measurement of the absorbance of the sample caused by undesired thermal radiation from the sample itself, first and second sectors are used for division and recombination of beam paths and coordinated such that a detector which receives a beam along the combined beam path produces output signals consisting of components having a frequency f associated with the cycle of operation of the sectors and components having a frequency 2f, those components having frequencies f and 2f are independently derived out of the detector output signals, and the ratio of the components is computed, thereby obtaining the ratio of intensity of sample beam to reference beam independent of the undesired thermal radiation.

12 Claims, 11 Drawing Figures

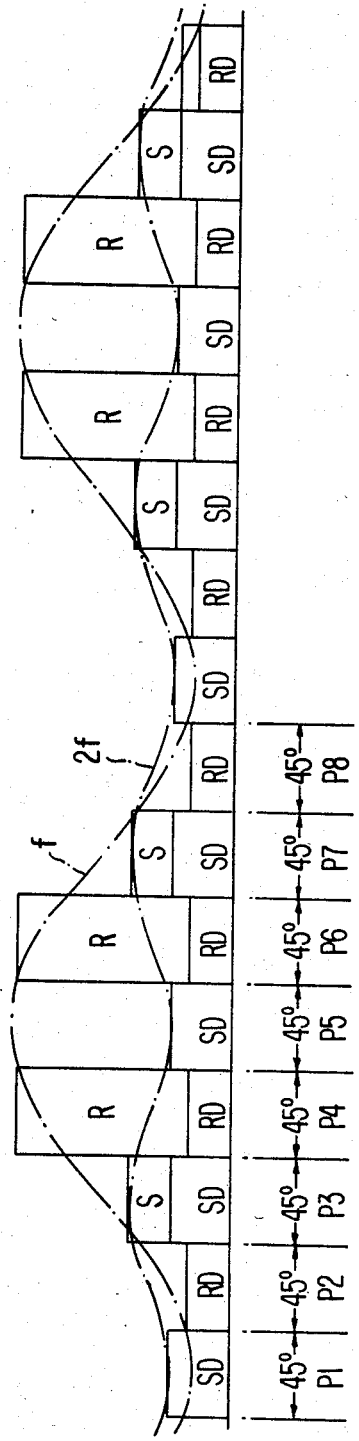
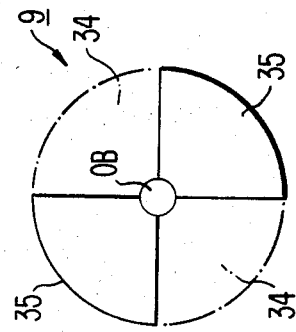
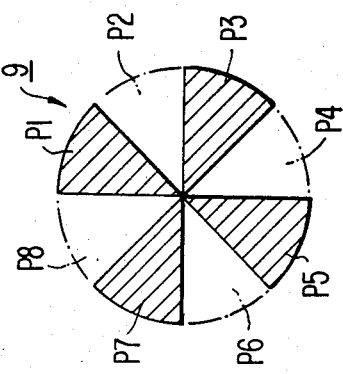
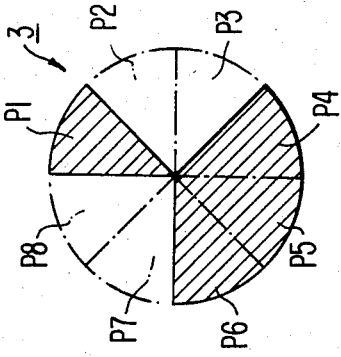

SPECTROPHOTOMETER

BACKGROUND OF THE INVENTION

This invention relates to double-beam spectrophotometers, and more particularly, to spectrophotometers capable of spectral analysis in the infrared region while eliminating a measurement error caused by undesired radiation.

As is well known in the art, the double-beam spectrophotometers measure the transmittance of a sample by alternately directing a beam of infrared radiation to the sample and a reference or standard material (or an empty cell), detecting the intensity of the sample beam transmitted by the sample and the reference or standard beam transmitted by the reference or standard material, and comparing the sample beam intensity with the reference beam intensity, with the resultant ratio giving the transmittance or absorbance of the sample.

Among such spectrophotometers, thermal infrared detectors such as vacuum thermocouple detectors are often used to carry out analysis in the infrared region. Since both the sample material under analysis and the reference material themselves emit thermal radiation in the infrared region dependent on the ambient temperature and elevated temperatures resulting from illumination, the detector receives the infrared radiation in which the thermal radiation of the sample or reference material itself overlaps the light transmitted by the sample or reference material. Therefore, the output signals of the detector indicative of the intensity of sample and reference beams involve false signals due to thermal radiation. Comparing such detector output signals with each other without any compensation will result in an inaccurate representation of the transmittance of the sample. Particularly when the sample under analysis is at high temperatures, its thermal radiation becomes intense to increase the level of a false signal, thereby introducing a significant error in the measured transmittance of the sample, which is not reliable.

To avoid such inconvenience, so-called emissionless spectrophotometers have been proposed which are adapted to eliminate the influence of undesired radiation.

One typical example is the double-beam spectrophotometer disclosed in Japanese Patent Publication No. SHO 42-23555 (invented by Shigeo Minami, published on Nov. 14, 1967). This spectrophotometer applied a double-chopping system to the well-known optical null balance system to eliminate the influence of unnecessary radiation. In the optical null balance system, generally, a mechanical beam attenuator comprising a wedge-shaped stop or optical wedge driven by a serve motor is inserted in the path of reference beam, the sample beam and the reference beam attenuated by the mechanical attenuator are alternately interrupted by means of a chopper, an alternating current signal is derived out which has an amplitude proportional to the difference between the reference beam intensity and the sample beam intensity, the signal is used as an error signal in a closed loop, and the attenuator is automatically adjusted so that the value of the error signal may become zero. When the attenuator is adjusted in this way, the magnitude of attenuation or the distance of movement of the optical wedge corresponds to the absorbance of the sample, and consequently, changes in the absorbance of the sample can be measured by recording the distance of movement of the attenuator wedge. In such spectrophotometers based on the optical null balance system, according to the invention of the above-mentioned publication, an auxiliary chopper is inserted between the sample and reference cells and the light source in addition to the above-mentioned chopper (main chopper) between the sample and reference cells and the detector. The main chopper switches the beam paths at a given frequency $f_1$ while the auxiliary chopper is driven so as to switch the beam paths at frequency $f_2$ lower than frequency $f_1$. The detector includes a series connection of an amplifier for amplifying a signal having frequency $f_1$, a synchronous rectifier in synchronism with the main chopper, another amplifier for amplifying a signal having frequency $f_2$, and another synchronous rectifier in synchronism with the auxiliary chopper in this order. The output of this series circuit, which is used to drive the servo motor of the attenuator, is a signal which is proportional to the difference between the light transmitted by the reference material and the light transmitted by the sample and free of a signal component due to undesired radiation. As a result, there can be obtained a correct absorbance of the sample free of an error induced by undesired radiation.

The above-mentioned spectrophotometers based on the optical null balance system have several drawbacks described below. First of all, since the accuracy of transmittance largely depends on the mechanical accuracy of the attenuator itself as well as the associated drive system, the spectrophotometer is difficult to exhibit highly accurate and stable performance. In connection with this, due to fluctuations in rotation of a driving servo motor for moving a wedge-shaped stop commonly used in the attenuator, error in linearity of a potentiometer for detecting the position of the wedge-shaped stop, and other factors, the distance of movement of the stop is not always proportional to the magnitude of attenuation, often resulting in low accuracy of transmittance measurement. Further, the inclusion of the optical system in the servo loop results in a complicated and expensive apparatus which handles signals in a complicated way and has poor response. In the case of a sample having high absorbance, the sample beam intensity approximates to zero, and accordingly, the reference beam intensity is also attenuated to a level near zero, resulting in reduced loop gain and reduced reliability. In addition, the attenuator itself is reduced in accuracy when the magnitude of attenuation is very high, that is, when the sample has very high absorbance. These undesirably causes a substantial reduction in accuracy of measurement of a high absorbance sample.

Another example of the double-beam spectrophotometers having eliminated the problem of measurement error caused by the undesired radiation of the sample itself is one disclosed in Japanese Patent Publication No. SHO 47-3798 (invented by Michael Allan Ford, published on Feb. 2, 1972). This meter is based on the so-called double-chopping phase control system and includes a split chopper for dividing a beam of light from a light source between sample and reference paths and a recombination chopper for recombining the sample and reference beam paths. The split chopper is in the form of a disc consisting of four quadrants among which one quadrant is transparent, another adjoining quadrant is a reflective region, and the remaining two quadrants are light-shielding regions. The recombination chopper is in the form of a disc divided into two semi-circular transparent and reflective regions. The recombination chopper is rotated at a speed twice the rotation speed of the split chopper. With such choppers cooperated, the detector develops four output signals of $S+S_0$, $R+R_0$, $S_0$, and $R_0$ in this order with a mutual phase difference of 90 degrees, provided that S represents the light beam transmitted by the sample, $S_0$ represents the thermal radiation of the sample, R represents the light beam transmitted by the reference material, and $R_0$ represents the thermal radiation of the reference material. These signals may be isolated and rectified with a phase difference of 90 degrees by means of a synchronous rectifier comprising, for example, a slip ring and a brush, thereby producing S and R signals both free of $S_0$ and $R_0$. The transmittance or absorbance of the sample is given as the ratio of these signals. However, the spectrophotometers using the phase control system have the following problems.

When wavelength scanning is generally carried out in spectral analysis, an output waveform of the detector in one cycle sometimes loses its symmetry in a wavelength region where the sample shows high absorbance. In addition, absorption by atmospheric water vapor and carbon dioxide has probably an influence on both the reference and sample beams, distorting the output waveform of the detector in one cycle. In the case of the phase discrimination system, such a distortion of the output waveform largely affects the phase, eventually resulting in a significant error in measurement. This problem will be further explained below. For high absorbance samples, absorbance varies very rapidly during wavelength scanning, resulting in a graded sample beam intensity in one cycle. Since a detector, particularly a thermal infrared detector such as a thermocouple has a large time constant, its output signal appears to have the effect of integrating the intensity waveform of incident light. If the sample beam intensity in one cycle has a gradient as mentioned above, the output waveform is off-centered from the input waveform of the sample beam intensity so that the phase difference between the sample and reference beam intensity components in the output is shifted from 90 degrees, resulting in an error. Also, absorption by atmospheric water vapor and carbon dioxide has an influence on the intensity waveform of incident light to the detector to distort an output signal of the detector to give rise to a similar phase shift, resulting in an error in measurement.

In the case of the phase discrimination system spectro-photometer, if dust deposits on slits in the paths for reference and sample beams and any obstructions in proximity to the beam paths partially intercept beams or mechanical positioning of slits is inaccurate, then the rise or fall of a waveform representative of the intensity of an incident beam to the detector is shifted from the originally set phase, and thus the corresponding output waveform of the detector is deviated, also resulting in an error in measurement. Furthermore, the two choppers mentioned above must be accurately synchronized so as not to leave any phase difference, but in practice, such accurate synchronization is very difficult to achieve without troublesome adjustment.

Accordingly, it is an object of the present invention to provide an emissionless spectrophotometer based on the frequency component detecting system which has eliminated the drawbacks unavoidably associated with prior art emissionless spectrophotometers based on the optical null balance system and the phase control system mentioned above.

SUMMARY OF THE INVENTION

According to the present invention, there is provided a double-beam spectrophotometer comprising
a source for emitting a beam of light,
a first sector for alternately distributing the beam from said source between reference and sample beam paths to form reference and sample beams, respectively,
reference and sample cells located in the reference and sample beam paths, respectively,
a second sector disposed substantially at the crossing of the reference and sample beam paths for guiding the reference and sample beams into a common beam path,
a monochromator disposed in the common beam path,
a detector located downstream of said monochromator for detecting the intensity of the monochromatic light from said monochromator, and
signal processing means electrically connected to said detector for processing an output signal of said detector.

The first and second sectors are coordinated such that said detector receives from said monochromator the following eight light inputs (a) to (h):
(a) radiant light from the reference cell which does not receive the light beam from the source,
(b) radiant light from the sample cell which does not receive the light beam from the source,
(c) the light beam transmitted by the reference cell which receives the light beam from the source,
(d) the light beam transmitted by the sample cell which receives the light beam from the source,
(e) radiant light from the reference cell which does not receive the light beam from the source,
(f) the light beam transmitted by the sample cell which receives the light beam from the source,
(g) the light beam transmitted by the reference cell which receives the light beam from the source, and
(h) radiant light from the sample cell which does not receive the light beam from the source,
in this sequence with a phase difference of 45 degrees in one cycle.

The signal processing means comprises
a first amplifier for amplifying that component of the output signal of said detector which has a frequency f corresponding to said cycle,
a first synchronous rectifier for synchronously rectifying the output of said first amplifier,
a second amplifier for amplifying that component of the output signal of said detector which has a frequency 2f twice the frequency f,
a second synchronous rectifier for synchronously rectifying the output of said second amplifier, and
divider means for computing the ratio of the output of said second rectifier to the output of said first rectifier.

BRIEF DESCRIPTION OF THE DRAWINGS

The above and other objects, features, and advantages of the present invention will be more fully understood by reading the following description when taken in conjunction with the accompanying drawings, in which:

FIG. 8 is a diagram showing output signals of the detector in another preferred embodiment;

FIGS. 9 and 10 are equivalent representations of transparent and reflective regions of the first and second sectors which are arranged to produce output signals as shown in FIG. 8; and FIG. 11 is a schematic view of the second sector in a further preferred embodiment.

DESCRIPTION OF THE PREFERRED EMBODIMENTS

Figure 1:
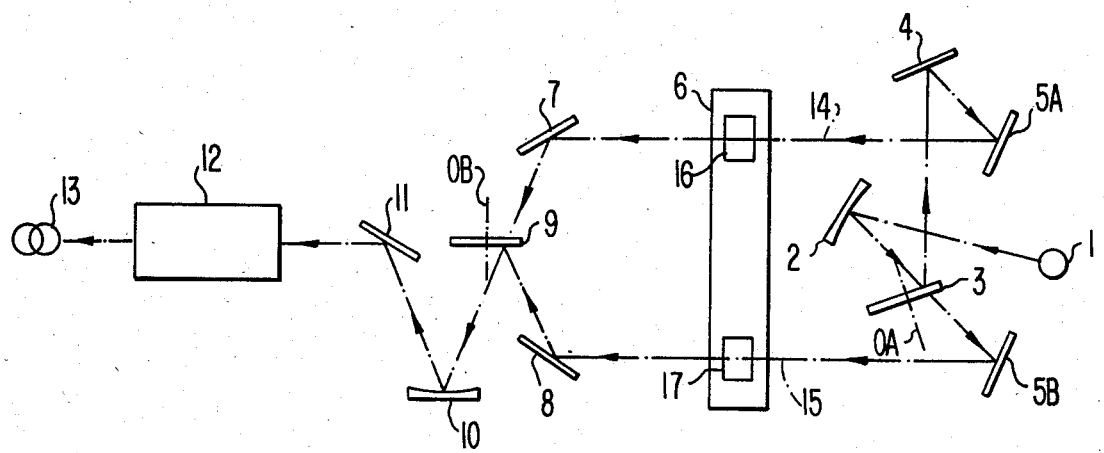
FIG. 1 is a block diagram of an optical system employed in the spectrophotometer of the present invention.
Figure 2:
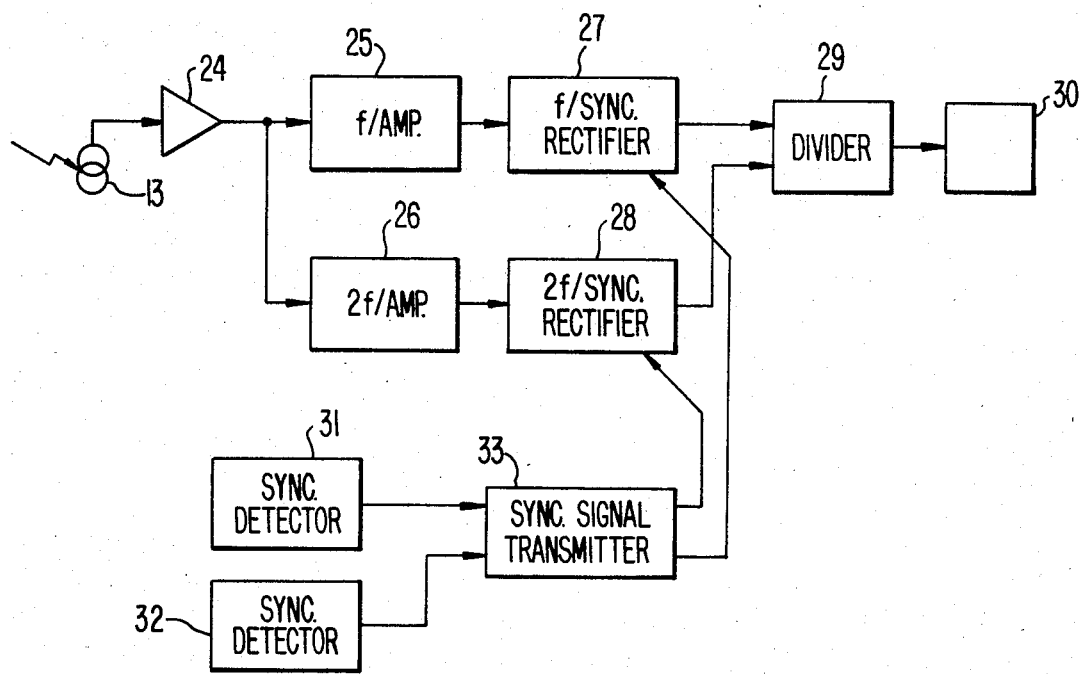
FIG. 2 is a block diagram of an electrical processing system employed in the spectrophotometer.

One preferred embodiment of the double-beam spectrophotometer according to the present invention will be described with reference to FIGS. 1 to 7. Referring to FIGS. 1 and 2, there are illustrated in block diagram an optical system and an electrical processing system involved in the spectrophotometer of the present invention. First, the optical system of the spectrophotometer of the present invention will be described in detail.

Referring to FIG. 1, a source 1 of infrared radiation in the form of a globar lamp and Nernst lamp emits a beam of infrared radiation toward a concave mirror 2 by which the beam is reflected to enter a first rotary sector 3 where the beam is alternately divided or distributed between two beam paths. The first sector 3 has reflective and transparent regions arranged in a particular pattern as will be described later. The light beam reflected by the first sector 3 is reflected by plane mirrors 4 and 5A to travel along a reference beam path 14 to form a reference beam, whereas the transmitted light beam from the first sector is reflected by a plane mirror 5B to travel along a sample beam path 15 to form a sample beam. The beams travelling along the reference and sample beam paths 14 and 15 enter reference and sample cells 16 and 17 supported in a cell holder 6 and aligned with the reference and sample beam paths, respectively, and are then reflected by plane mirrors 7 and 8. A second sector 9 is positioned substantially at the crossing of the thus deflected beam paths. The reference and sample beams enter the second sector 9 where they are guided into a common beam path. More specifically, the second sector 9 also has reflective and transparent regions arranged in a particular pattern as will be described later in detail. The reference beam passing through the second sector 9 and the sample beam reflected by the second sector 9 alternately appear in the common beam path. The light beam from the second sector 9 is focused to an incident slit of a monochromator 12 through a concave mirror 10 and a plane mirror 11. The light beam is spectrally isolated by the monochromator 12 into monochromatic light which in turn, enters a detector 13 in the form of a thermocouple where it is converted into an electrical signal.

The first and second sectors 3 and 9 are rotated about their axes OA and OB perpendicular to their major surface by drive means such as a motor (not shown), and incident light impinges on each sector at a point off the center.

Figure 3:
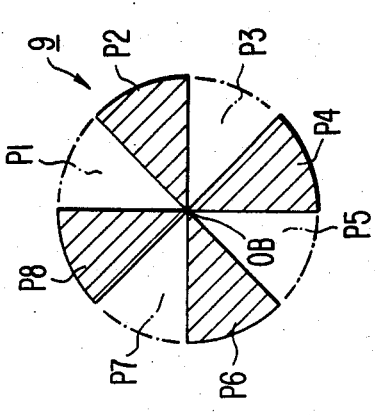
FIGS. 3 and 4 are schematic views of the first and second sectors used in one preferred embodiment of the invention, respectively.

The first sector 3 is in the form of a phantom disc which consists of, for example, as shown in FIG. 3, a first sectoral transparent or cut-out region 18 having a central angle of 45 degrees with respect to the axis of rotation OA and allowing incident light to pass therethrough, a second sectoral reflective or mirror region 19 having a central angle of 90 degrees and reflecting incident light, a third sectoral transparent or cut-out region 20 having a central angle of 135 degrees and allowing incident light to pass therethrough, and a fourth sectoral reflective or mirror region 21 having a central angle of 90 degrees and reflecting incident light, the first to fourth sectoral regions being circumferentially arranged about the axis of rotation OA in this order.

Figure 4:
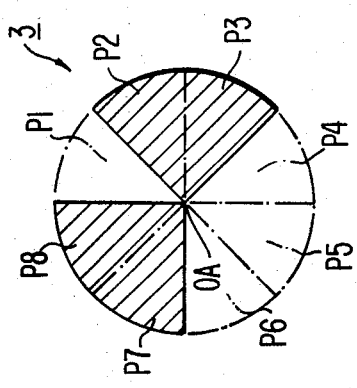

The second sector 9 is in the form of a phantom disc which consists of, for example, as shown in FIG. 4, a semi-circular reflective or mirror region 22 having a central angle of 180 degrees with respect to the axis of rotation OB and reflecting incident light, and another semi-circular transparent or cut-out region 23 having a central angle of 180 degrees and allowing incident light to pass therethrough.

Figure 5:
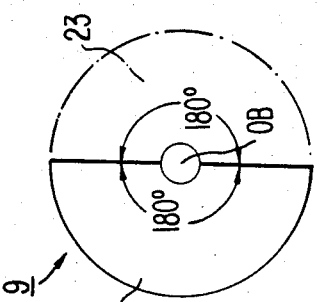
FIGS. 5 and 6 are equivalent representations of transparent and reflective regions of the first and second sectors, helpful to identify output signals of the detector.
Figure 6:
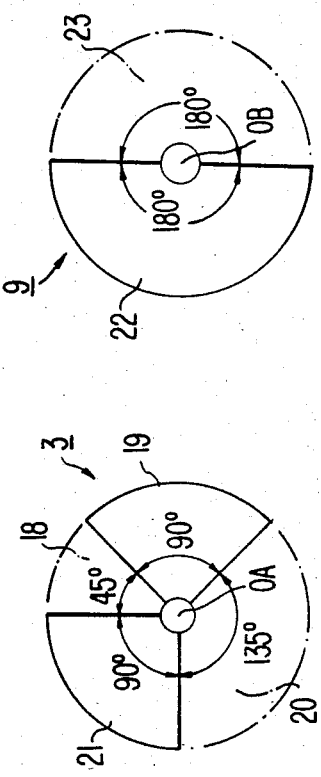
Figure 7:
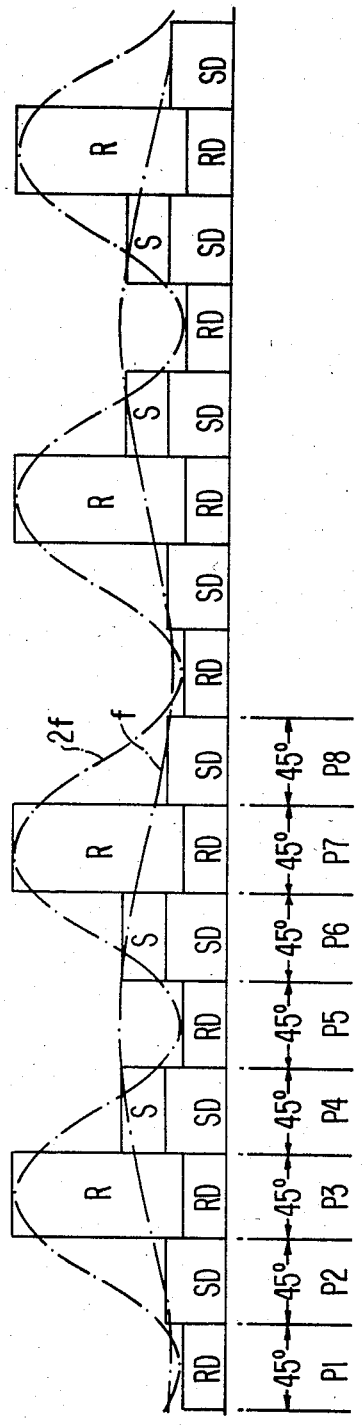
FIG. 7 is a diagram showing output signals of the detector.

In carrying out analytical measurement using the above-described optical system, the reference cell 16 may be filled with a reference material or kept empty and the sample cell 17 is filled with a sample to be analyzed. The first and second sectors 3 and 9 are synchronously rotated at a speed ratio of 1:4. More specifically, the first transparent region 18 of the first sector 3 is first positioned in register with the transparent region 23 of the second sector 9, and the second sector 9 makes four revolutions while the first sector 3 makes one revolution. For one revolution of the first sector 3, the sequence of transmission and reflection provided by the first and second sectors 3 and 9 can be shown as equivalent representations in FIGS. 5 and 6. Consequently, the detector 13 develops sequential signals as shown in FIG. 7. In FIGS. 5 and 6, blank regions represent transmission and hatched regions represent reflection.

The signals sequentially developed by the detector 13 as shown in FIG. 7 will be described in more detail. As understood from FIGS. 5 and 6, eight signals are sequentially developed with a phase difference of 45 degrees during one revolution of the first sector 3. In a first 45° zone P1, the light beam from the source 1 passes through the first sector 3 to form a sample beam (15). At this point, the second sector 9 presents a transparent region so that the sample beam (15) cannot reach the monochromator 12 while dark light from the reference cell 16, which does not receive a light beam from the source, enters the monochromator 12 which develops a signal representative of reference dark RD. The reference dark RD consists essentially of undesirable radiant light from the reference material in the reference cell 16. In a second 45° zone P2, the light beam from the source 1 is reflected by the first sector 3 to form a reference beam (14). At this point, the second sector 9 presents a reflective region so that the reference beam (14) cannot reach the monochromator 12 while dark light from the sample cell 17, which does not receive a light beam from the source, enters the monochromator 12 which develops a signal representative of sample dark SD. The sample dark SD consists essentially of undesirable radiant light from the sample in the sample cell 17. In a third 45° zone P3, the light beam from the source 1 is reflected by the first sector 3 to form a reference beam (14). At this point, the second sector 9 presents a transparent region so that the reference beam (14) along with reference dark radiation enters the monochromator 12 which develops a signal representative of reference R plus reference dark RD. In a fourth 45° zone P4, the light beam from the source 1 passes through the first sector 3 to form a sample beam (15). At this point, the second sector 9 presents a reflective region so that the sample beam (15) along with sample dark radiation enters the monochromator 12 which develops a signal representative of sample S plus sample dark SD. Thereafter, in the following zones P5, P6, P7, and P8, signals representative of RD, S+SD, R+RD, and SD are sequentially developed as shown in FIG. 7, totalling to eight signals in one cycle. It should be noted that for convenience of description, the intensity of the beam transmitted by the reference material or cell is referred to as reference R, the intensity of the beam transmitted by the sample material or cell is referred to as sample S, the intensity of dark radiant light from the reference material or cell itself is referred to as reference dark RD, and the intensity of dark radiant light from the sample material or cell itself is referred to as sample dark SD.

Provided that the first sector 3 is rotated at a frequency f and the second sector 9 is rotated at a frequency 4f, the detector 13 develops f sets of the eight signals mentioned above per unit time. During operation of the optical system, the output of the detector 13 involves a signal having the frequency 2f corresponding to reference R and a signal having the frequency f corresponding to sample S as seen from waveforms interconnected by dot-and-dash lines in FIG. 7. It will be understood that the signal at frequency 2f has an amplitude of $R=(R+RD)-RD$ and the signal at frequency f has an amplitude of $S=(S+SD)-SD$, which means that the dark components corresponding to undesired radiant light from the reference and sample materials may be removed.

Next, the electrical processing system for computing the S/R ratio, that is, the percent transmission of the sample material on the basis of outputs of the detector mentioned above will be described with reference to FIG. 2. The electrical processing system connected to the detector 13 includes a pre-amplifier 24 for amplifying the output signal of the detector 13, and a first amplifier 25 connected to the preamplifier 24 for amplifying that component of the signal which corresponds to frequency f, and a second amplifier 26 also connected to the pre-amplifier 24 for amplifying that component of the signal which corresponds to frequency 2f, whereby the components having frequencies f and 2f are independently amplified. The outputs of the first and second amplifiers 25 and 26 are rectified by first and second synchronous rectifiers 27 and 28 set to frequencies f and 2f, respectively, and then supplied to a divider 29 where the ratio of these outputs is computed. It should be noted that since the f-component output of the first synchronous rectifier 27 corresponds to sample S, that is, the intensity of the beam transmitted by the sample material free of the sample dark component (SD) and the 2f-component output of the second synchronous rectifier 28 corresponds to reference R, that is, the intensity of the beam transmitted by the reference material free of the reference dark component (RD), the output of the divider 29 directly corresponds to the S/R ratio free of a false signal component resulting from the undesired radiant light. The value of this output is indicated on an indicator/recorder 30.

As shown in FIG. 2, the synchronous rectifiers 27 and 28 set to frequencies f and 2f receive sync signals from synchronous detectors 31 and 32 associated with the first and second sectors 3 and 9 via a common sync signal transmitter 33. The synchronous detectors may be any desired one of well-known type, for example, photocouplers and the detailed description and illustration are omitted.

Although the second sector 9 is provided with a reflective surface on the side on which the light beam along the sample beam path 15 is incident in the embodiment shown in FIG. 1, inversely, the second sector may be provided with a reflective surface on the side on which the light beam along the reference beam path 14 is incident and the concave mirror 10 and the plane mirror 11 may be re-arranged such that the monochromator 12 may receive reflected light from the reference beam path and transmitted light from the sample beam path. In this case, however, inversely to the order shown in FIG. 6, the phase of rotation of the second sector 9 must be controlled such that regions P1, P3, P5, and P7 are reflective regions and regions P2, P4, P6, and P8 are transparent regions.

It is only required for the first sector 3 that regions P1 and P5 do not substantially allow the light beam from the source to enter the reference beam path. Instead of making regions P1 and P5 transparent as shown in FIG. 5, these regions P1 and P5 may be a non-reflective screening region which does not allow the beam from the source to be transmitted to the sample beam path or substantially reflected to the reference beam path. Also, it is only required for the first sector 3 that regions P2 and P8 do not allow the light beam from the source to enter the sample beam path. Instead of making regions P2 and P8 reflective as shown in FIG. 5, these regions P2 and P8 may be a nonreflective screening region which does not allow the beam from the source to be transmitted to the sample beam path or substantially reflected to the reference beam path. In these cases, the detector produces the same outputs as shown in FIG. 7.

Next, another preferred embodiment of the spectrophotometer according to the present invention will be described. Although the reference and sample beam paths 14 and 15 are drawn on the upper and lower sides in the first embodiment shown in FIG. 1, the beam paths may be replaced with each other, that is, the reference and sample cells 16 and 17 may be replaced with each other, for example, by rotating the cell holder 6 an angle of 180 degrees. In this case, however, output signals of the detector 13 contain reference and sample components in the inverse order to those signals in the first embodiment. There are developed eight signals of SD, RD, S+SD, R+RD, SD, R+RD, S+SD, and RD in this order with a phase difference of 45° in one cycle as shown in FIG. 8. As seen from FIG. 8, the curve having frequency f corresponds to reference R and the curve having frequency 2f corresponds to sample S. Therefore, in this embodiment, the S/R ratio is obtained in the divider 29 by computing the ratio of 2f-component to f-component.

It should be understood that replacing the reference and sample beam paths 14 and 15 with each other is equivalent to replacing the transparent and reflective regions of the first sector 3 with each other with the arrangement of the beam paths 14 and 15 in the FIG. 1 unchanged, and at the same time, replacing the transparent and reflective regions of the second sector 9 with each other. In the latter case, regions P1, P4, P5, and P6 of the first sector 3 are made reflective regions which reflect the beam from the source to the reference beam path 14, and regions P2, P3, P7, and P8 are made transparent regions which transmit the beam from the source to the sample beam path 15 as shown in FIG. 9. Regions P1, P3, P5, and P7 of the second sector 9 are made reflective regions which reflect the beam along the sample beam path 15 to the monochromator, and regions P2, P4, P6, and P8 are made transparent regions which transmit the beam along the reference beam path 14 to the monochromator as shown in FIG. 10. Furthermore, regions P1 and P5 of the first sector 3 may be non-reflective screening regions as they are only required not to allow the beam from the source to enter the sample beam path 15. Similarly, regions P2 and P8 of the first sector 3 may be non-reflective screening regions as they are only required not to allow the beam from the source to enter the reference beam path 14.

In the above embodiments, the second sector 9 is used which consists of a semi-circular transparent region and the remaining semi-circular reflective region, although the configuration of the second sector is not limited thereto. For example, as shown in FIG. 11, the second sector 9 may consist of two opposed transparent regions 34 and two opposed reflective regions 35 all having a central angle of 90° with respect to the central axis. Since the sector consists of four quadrants rather than two semi-circles in this case, the ratio of rotation speed of the first sector to the second sector should be 1:2 rather than 1:4 in order to obtain the output signals shown in FIG. 7 from the detector. Furthermore, the second sector 9 may be a disc having transparent regions and reflective regions arranged about the central axis, each region having an equal central angle of 45 degrees. In this case, the first and second sectors 3 and 9 may be rotated at a speed ratio of 1:1. If the reference cell and the sample cell are replaced with each other, there are obtained the output signals shown in FIG. 8 from the detector as described previously.

BENEFITS OF THE INVENTION

As seen from the foregoing, the present invention provides an emissionless spectrophotometer which is free of the drawbacks inherently associated with the prior art optical null balance and phase control systems because the spectrophotometer is designed so as to directly determine the S/R ratio electrically on the basis of the frequency component detection system in which first and second sectors each having transparent and reflective regions in a given pattern are used for division and recombination of beam paths, respectively, the first and second sectors are synchronously rotated at a given speed ratio, and signal components having frequencies f and 2f are independently derived out.

Although the spectrophotometer of the optical null balance system experiences substantial reductions in measurement accuracy due to finishing accuracy of an optical attenuator, rotational fluctuation in driving of the attenuator, and errors in the linearity of a potentiometer for detecting the position of the attenuator, the spectrophotometer of the invention has eliminated such drawbacks. The spectrophotometer of the invention based on the direct ratio determining system does not need a serve loop system and is thus relatively simple to process signals and to construct.

The spectrophotometer of the invention is also free of the disadvantages of the phase control system that inaccurately aligned components and foreign matters more or less eclipse a beam of light to change the energy thereof to deform the waveform of beam intensity, resulting in a phase shift, generating noise, and reducing the linearity. As the phase shift caused by a change of energy distribution due to eclipse of light beam does not affect the linearity in the system of the present invention, minimal noise results from such a phase shift caused by an energy change. A certain distribution of energy in the light beam makes it difficult to find accurately 90° shifted phases of the sample and reference beams in the phase control system, but the present invention avoids such troublesome operation.

What I claim is:
1. A double-beam spectrophotometer comprising
   a source for emitting a beam of light,
   a first sector for alternately distributing the beam from said source between reference and sample beam paths to form reference and sample beams, respectively,
   reference and sample cells located in the reference and sample beam paths, respectively,
   a second sector disposed substantially at the crossing of the reference and sample beam paths for guiding the reference and sample beams into a common beam path,
   a monochromator disposed in the common beam path,
   a detector located downstream of said monochromator for detecting the intensity of the monochromatic light from said monochromator, and
   signal processing means electrically connected to said detector for processing an output signal of said detector,
   wherein said first and second sectors are coordinated such that said detector receives from said monochromator the following eight light inputs (a) to (h):
   (a) radiant light from the reference cell which does not receive the light beam from the source,
   (b) radiant light from the sample cell which does not receive the light beam from the source,
   (c) the light beam transmitted by the reference cell which receives the light beam from the source,
   (d) the light beam transmitted by the sample cell which receives the light beam from the source,
   (e) radiant light from the reference cell which does not receive the light beam from the source,
   (f) the light beam transmitted by the sample cell which receives the light beam from the source,
   (g) the light beam transmitted by the reference cell which receives the light beam from the source, and
   (h) radiant light from the sample cell which does not receive the light beam from the source,
   in this sequence with a phase difference of 45 degrees in one cycle, and
   said signal processing means comprises
   a first amplifier for amplifying that component of the output signal of said detector which has a frequency f corresponding to said cycle,
   a first synchronous rectifier for synchronously rectifying the output of said first amplifier,
   a second amplifier for amplifying that component of the output signal of said detector which has a frequency 2f twice the frequency f,
   a second synchronous rectifier for synchronously rectifying the output of said second amplifier, and divider means for computing the ratio of the output of said first rectifier to the output of said second rectifier.

2. The spectrophotometer according to claim 1 wherein
said first sector comprises a disc adapted to rotate about its axis and divided into the following eight regions having an equal central angle of 45° with respect to the axis:
a first region which does not substantially reflect the beam from the source to the reference beam path,
a second region which does not substantially transmit the beam from the source to the sample beam path,
a third region which reflects the beam from the source to the reference beam path,
a fourth region which transmits the beam from the source to the sample beam path,
a fifth region which does not substantially reflect the beam from the source to the reference beam path,
a sixth region which transmits the beam from the source to the sample beam path,
a seventh region which reflects the beam from the source to the reference beam path, and
an eighth region which does not substantially transmit the beam from the source to the sample beam path, and
said second sector comprises a disc adapted to rotate about its axis at a speed n times higher than the rotation speed of said first sector where n is an integer selected from 1, 2, and 4, said disc being alternately divided at an equal angle of 45°×n with respect to the axis into a region which transmits either one of the reference and sample beams to the monochromator and another region which reflects the other beam to the monochromator.

3. The spectrophotometer according to claim 2 wherein at least one of said first and fifth regions is a region which transmits the beam from the source to the sample beam path.

4. The spectrophotometer according to claim 2 wherein at least one of said first and fifth regions is a non-reflective screening region which does not allow the beam from the source to be transmitted to the sample beam path or substantially reflected to the reference beam path.

5. The spectrophotometer according to claim 2 wherein at least one of said second and eighth regions is a region which reflects the beam from the source to the reference beam path.

6. The spectrophotometer according to claim 2 wherein at least one of said second and eighth regions is a non-reflective screening region which does not allow the beam from the source to be transmitted to the sample beam path or substantially reflected to the reference beam path.

7. A double-beam spectrophotometer comprising
a source for emitting a beam of light,
a first sector for alternately distributing the beam from said source between reference and sample beam paths to form reference and sample beams, respectively,
reference and sample cells located in the reference and sample beam paths, respectively,
a second sector disposed substantially at the crossing of the reference and sample beam paths for guiding the reference and sample beams into a common beam path,
a monochromator disposed in the common beam path,
a detector located downstream of said monochromator for detecting the intensity of the monochromatic light from said monochromator, and
signal processing means electrically connected to said detector for processing an output signal of said detector,
wherein said first and second sectors are coordinated such that said detector receives from said monochromator the following eight light inputs (a) to (h):
(a) radiant light from the sample cell which does not receive the light beam from the source,
(b) radiant light from the reference cell which does not receive the light beam from the source,
(c) the light beam transmitted by the sample cell which receives the light beam from the source,
(d) the light beam transmitted by the reference cell which receives the light beam from the source,
(e) radiant light from the sample cell which does not receive the light beam from the source,
(f) the light beam transmitted by the reference cell which receives the light beam from the source,
(g) the light beam transmitted by the sample cell which receives the light beam from the source, and
(h) radiant light from the reference cell which does not receive the light beam from the source,
in this sequence with a phase difference of 45 degrees in one cycle, and
said signal processing means comprises
a first amplifier for amplifying that component of the output signal of said detector which has a frequency f corresponding to said cycle,
a first synchronous rectifier for synchronously rectifying the output of said first amplifier,
a second amplifier for amplifying that component of the output signal of said detector which has a frequency 2f twice the frequency f,
a second synchronous rectifier for synchronously rectifying the output of said second amplifier, and
divider means for computing the ratio of the output of said second rectifier to the output of said first rectifier.

8. The spectrophotometer according to claim 7 wherein
said first sector comprises a disc adapted to rotate about its axis and divided into the following eight regions having an equal central angle of 45° with respect to the axis:
a first region which does not substantially transmit the beam from the source to the sample beam path,
a second region which does not substantially reflect the beam from the source to the reference beam path,
a third region which transmits the beam from the source to the sample beam path,
a fourth region which reflects the beam from the source to the reference beam path,
a fifth region which does not substantially transmit the beam from the source to the sample beam path, a sixth region which reflects the beam from the source to the reference beam path, a seventh region which transmits the beam from the source to the sample beam path, and an eighth region which does not substantially reflect the beam from the source to the reference beam path, said second sector comprises a disc adapted to rotate about its axis at a speed n times higher than the rotation speed of said first sector where n is an integer selected from 1, 2, and 4, said disc being alternately divided at an equal angle of 45°×n with respect to the axis into a region which transmits either one of the reference and sample beams to the monochromator and another region which reflects the other beam to the monochromator.

9. The spectrophotometer according to claim 8 wherein at least one of said first and fifth regions is a region which reflects the beam from the source to the reference beam path.

10. The spectrophotometer according to claim 8 wherein at least one of said first and fifth regions is a non-reflective screening region which does not allow the beam from the source to be transmitted to the sample beam path or substantially reflected to the reference beam path.

11. The spectrophotometer according to claim 8 wherein at least one of said second and eighth regions is a region which transmits the beam from the source to the sample beam path.

12. The spectrophotometer according to claim 8 wherein at least one of said second and eighth regions is a non-reflective screening region which does not allow the beam from the source to be transmitted to the sample beam path or substantially reflected to the reference beam path.

* * * * *